United States Patent

Huftel et al.

[11] 4,317,535
[45] Mar. 2, 1982

[54] STAPLER WITH TAPERED ANVIL

[75] Inventors: Terrance D. Huftel, Hudson Township, St. Croix County, Wis.; Lester B. Odegaard, Afton, Minn.; Thomas K. Rasmussen, Roberts, Wis.

[73] Assignee: Minnesota Mining and Manufacturing Company, St. Paul, Minn.

[21] Appl. No.: 149,901

[22] Filed: May 15, 1980

[51] Int. Cl.³ .............................................. B25C 5/04
[52] U.S. Cl. ............................ 227/19; 128/334 R; 227/83; 227/DIG. 1
[58] Field of Search ............ 227/19, 83, 120, DIG. 1; 128/334 R

[56] References Cited

U.S. PATENT DOCUMENTS

| | | | |
|---|---|---|---|
| 4,202,480 | 5/1980 | Annett | 227/19 X |
| 4,256,251 | 3/1981 | Moshofsky | 227/19 X |

*Primary Examiner*—Howard N. Goldberg
*Assistant Examiner*—Fred A. Silverberg
*Attorney, Agent, or Firm*—Cruzan Alexander; Donald M. Sell; William L. Huebsch

[57] ABSTRACT

An anvil in a stapler around which generally U shaped staples are bent into a generally rectangular shape, which anvil has edge surfaces outwardly tapered from a guide surface from which the anvil projects, which tapered edge surfaces help maintain the staples adjacent and in alignment with the guide surface as they are bent closed.

3 Claims, 7 Drawing Figures

STAPLER WITH TAPERED ANVIL

TECHNICAL FIELD

This application relates to structures for maintaining staples in proper alignment as they are closed around an anvil, and in one important aspect to such structures on staplers of the type used in the medical field to join disunited tissue.

BACKGROUND ART

The art is repleat with staplers that close a generally U-shaped staple by bending spaced parts of a central portion of the staple around the surfaces of an anvil so that projecting legs of the staple will engage and join adjacent materials (such as portions of disunited skin) adjacent the anvil, whereupon the anvil can be withdrawn from within the closed, generally rectangular, staple which will then hold the materials together.

Typically, the anvil in such a stapler projects from a planar guide surface for the staple, and has surfaces around which a staple is to be bent disposed generally at right angles to the guide surfaces. These anvil surfaces include opposite edge surfaces spaced at a distance corresponding to the distance between the spaced parts of the staple to be bent, and a contact surface extendng transverse of the passageway between the edge surfaces adopted to engage the central portion of the staple between the spaced parts to be bent. Means are provided for positioning a staple at the anvil with the central portion of the staple extending across the contact surface, the parts of the staple to be bent during closing at the edges where the contact surface and edge surfaces meet, and the legs of the staple projecting along the edge surfaces and the guide surface. A rim having a side surface positioned along the guide surface has an end portion adjacent the anvil, which end portion has spaced tip portions with a generally U-shaped opening therebetween defined by end surfaces on the ram disposed generally at right angles to the guide surface. The end surfaces on the ram include an innermost surface generally parallel and opposed to the contact surface on the anvil, and opposed side surfaces generally parallel to the edge surfaces on the anvil and spaced apart a distance exceeding the distance between the edge surfaces by about twice the thickness of the central portion of a staple. The ram is mounted on the housing for movement from a first position affording positioning a staple along the guide surface adjacent the anvil, to a formed position with the side surfaces of the ram opposite the edge surfaces of the anvil and the innermost surface of the ram adjacent the contact surface of the anvil to close the staple by bending its central portion around the anvil.

Such a stapler adapted for use in the medical field is described in U.S. patent application Ser. No. 14,911 filed Feb. 26, 1979 now U.S. Pat. No. 4,202,480. The stapler described in that application is activated by manually squeezing together toggle linkages on opposite sides of the path for the ram to move the ram to its formed position so that it will close the staple around the anvil.

While the staples described in that application normally work with good reliability, the possibility has existed that a staple could become displaced along the anvil away from the guide surface as the staple was clossed due, perhaps, to the staple being closed into a material it could not penetrate (such as metal) or other external forces. In extreme cases, such displacement could even cause the end surfaces of the plunger to become scored so that the scoring in the plunger would cause subsequent staples closed by the stapler to move away from the guide surface along the anvil, and thus not to be properly closed. While various approaches have been used to correct this problem such as hardening the end portion of the ram and/or longitudinally grooving the ram along its side surfaces to guide the portions of the staples bent around the anvil and prevent such scoring, or disposing the contact surface of the anvil at a slight acute angle with the guide surface to bias the central part of the staple to the intersection between the guide surface and the contact surface of the anvil, these approaches have either been expensive, have not been entirely successful in solving the problem, or have presented additional problems.

DISCLOSURE OF THE INVENTION

The present invention provides a simple effective solution to maintaining the staples along and in alignment with the guide surface as they are closed around the anvil, without the necessity of grooving or hardening the end portion of the ram or inclining the contact surface of the anvil.

According to the present invention, a stapler of the type described above has an anvil with edge surfaces adjacent the guide surface each disposed at an acute including angle of no less than about 80 degrees with respect to the guide surface of the stapler. Surprisingly, with such inclined side surfaces, a stapler being closed around the anvil by the end surfaces of the ram will remain generally in alignment with the guide surface until the staple is closed.

Preferably, the included angle between the edge surfaces and the guide surface is between 83 and 87 degrees with 85 degrees being the most preferred angle. Anvils having side surfaces disposed at an angle in that range reliably cause staplers closed about them to remain in alignment with the guide surface, while the anvils can still be easily withdrawn from within the closed staple.

BRIEF DESCRIPTION OF THE DRAWING

The present invention will be further described with reference to the accompanying drawing where like numbers refer to like parts in several views, and wherein.

DETAILED DESCRIPTION

Figure 1:
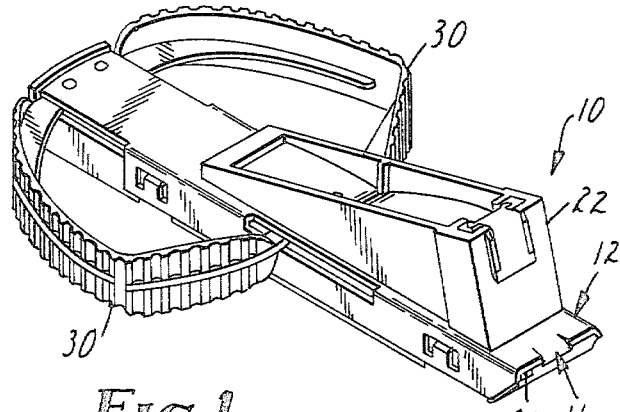
FIG. 1 is a perspective view of a stapler having an anvil according to the present invention.

Referring now to the drawing, there is shown a first embodiment of a stapler generally designated by the number 10 which includes an anvil 11 according to the present invention.

Except for the novel shape of the anvil 11, the stapler 10 has generally the same structure as that of the stapler disclosed in U.S. patent application Ser. No. 14,911, now U.S. Pat. No. 4,202,480 the disclosure whereof is incorporated herein by reference.

Briefly the stapler 10 comprises a housing 12 having a passageway partially defined by a guide surface 14

Figure 3:
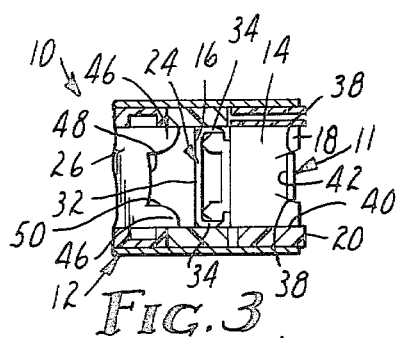
FIGS. 3 through 7 are fragmentary sectional views sequentially showing a ram in the stapler closing a staple about the anvil.
Figure 4:
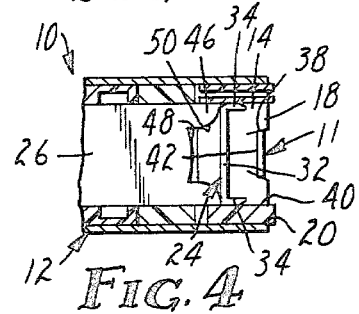
Figure 5:
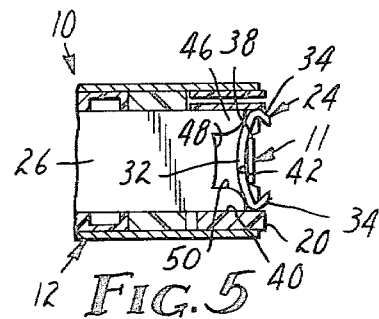
Figure 6:
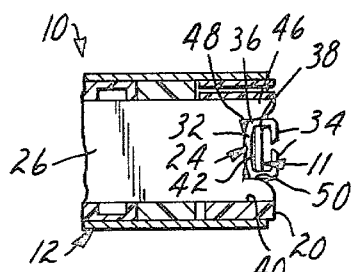
Figure 7:
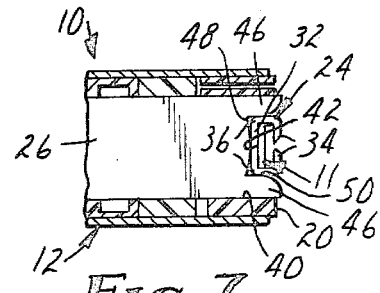

(FIG. 3) extending from an inlet opening 16 to an outlet opening 18 at an end 20 of the housing 12, which passageway is adapted to guide a single staple 24 moved from the inlet opening 16 to the anvil 11 at the outlet opening 18. A cartridge 22 provides means for biasing a stack of the staples 24 into the inlet opening 16. A ram 26 is mounted on the housing 12 for sliding movement from a load position (FIG. 3) with the ram 26 spaced from the inlet opening 16 to afford movement of one of the staples 24 into the passageway along the passageway with the ram 26 pushing the staple 24 toward and into engagement with the anvil 11 to a formed position at which the ram 26 has closed the staple 24 around the anvil 11 (FIG. 7), which anvil 11 is fixed to the housing 12 and projects from the guide surface 14 across the outlet opening 18 (FIGS. 4 through 6). The stapler 10 illustrated is particularly adapted for use by surgeons to join disunited skin portions into which the ends of the staples 24 formed around the anvil 11 are clenched, after which the anvil 11 is retracted from the central portion of the cleaned staple 24; which type of stapling is well known in the art.

Drive means manually activatable by manually pressing opposed flexible handle members 30 together is provided for propelling a drive member along the passageway to move the ram 26 from its load to its formed position, whereupon the resiliently flexible nature of the handle members 30 and a coil spring within the housing 12 (not shown) will cause the drive member to return to its initial position and means (not shown) for coupling the drive member to the ram 26 after the handle members 30 have been pressed together sufficiently to move the ram 26 to its formed position will return the ram 26 to its load position.

As is seen in FIGS. 3 through 6, the open generally U shaped stables 24 fed to the inlet opening 18 by the cartridge 22 each have a generally straight central portion 32 and a leg 34 projecting at a right angle from each end of its central portion 32 (FIGS. 3 and 4) and are bent closed into a generally rectangular shape (FIG. 6) around the anvil 11 by bending two predetermined spaced parts 36 of the central portion 32 of the staple 24. The anvil 11 has surfaces disposed generally at right angles to the guide surface 18 around which the staple 24 is formed by the ram 26, including opposite edge surfaces 38 spaced apart at a distance corresponding to the distance between the spaced parts 36 of the central portion of the staple 24 to be bent. Each edge surface 38 is spaced the same distance from the adjacent surface 40 of the housing 12, which housing surfaces 40 define edges of the passageway that help guide the legs 34 of the staple 24 as it is moved by the ram 26 from the inlet opening 16 to the anvil 11 so that the ram 26 and the surfaces of the housing 12 defining the passageway, including the surfaces 14 and 40 provide means for positioning the staple 24 at the anvil with its central portions 32 extending across a contact surface 42 of the anvil 11 which is transverse of the passageway, with the predetermined parts 36 of its central portion 32 to be bent positioned adjacent the edge surfaces 38 of the anvil 11, and with its legs 34 projecting along the edge surfaces 38 of the anvil 11 and the guide surface 14 at their intersections.

The ram 26 has a top side surface 44 (FIG. 2) positioned along the guide surface 14 on the housing, and has spaced tip portions 46 with a generally U shaped opening therebetween. The U shaped opening is defined by end surfaces on the ram 26 disposed generally at right angles to the guide surface 14 and including an innermost surface 48 generally parallel to and apposed to the contact surface 42 of the anvil 11, and apposed side surfaces 50 generally parallel to the edge surfaces 38 of the anvil 11 and each spaced from the adjacent edge surface 38 when the ram 26 is in its formed position by about the thickness of the central portion 32 of the staple 24.

When the stapler 10 is actuated by pressing the handle members 30 together, the tip portions 46 of the ram 26 push the staple 24 along the passageway (FIG. 4) where the staple 24 is guided with its legs 34 pointed toward the end 20 of the stapler 10 until the central portion 32 of the staple 24 engages the contact surface 42 of the anvil 11. Further movement of the ram 26 then causes the central portion 32 of the staple 24 to arc as the spaced tip portions 46 of the ram 26 pass the edges of the anvil 11 where the contact surface 42 and edge surfaces 38 meet (FIG. 3) and then to bend at the predetermined spaced parts 36 along the central portion 32 of the staple 24 around side edges of the anvil 11 so that the staple legs 34 move into end to end alignment with each other (FIG. 6) as the side surfaces 50 of the ram 26 start to move past the edge surfaces 38 of the anvil 11. Subsequently the innermost surface 48 on the ram 26 will engage and straighten the part of the staples central portion 32 that is adjacent the contact surface 42 by pressing it against that surface (FIG. 7), and the staple 24 is fully closed. The ram 26 may then be returned to its load position and the anvil 11 may be withdrawn from within the closed staple 24, whereupon the stapler 10 is ready for further use.

Figure 2:
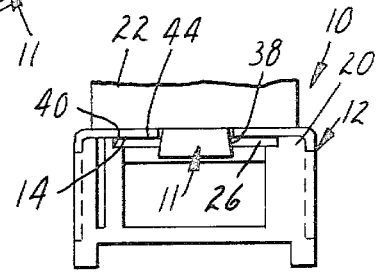
FIG. 2 is an enlarged fragmentary end view of the stapler of FIG. 1.

As is best seen in FIG. 2, the anvil 11 has a greater width between its edge surfaces 38 at its distal end than adjacent the guide surface 14 with the edge surfaces 38 of the anvil 11 adjacent the guide surface 14 each being being disposed at an acute included angle of no less than 80 degrees with respect to the guide surface 14 so that a staple 24 being closed around the anvil 11 by the end surfaces 48, 50 of the ram 26 will remain generally in alignment with the guide surface 14 until the staple is fully closed.

We claim:

1. In a stapler adapted to bend a generally U-shaped staple having a central portion and a leg projecting from each end of said central portion into a generally rectangular closed shape by bending two predetermined spaced parts of the central portion, said stapler comprising:

a housing having a passageway with an outlet opening, said passageway being partially defined by a planar guide surface;

an anvil fixed to said housing and projecting from said guide surface across said passageway at said outlet opening, said anvil having surfaces disposed generally at right angles to said guide surface including opposite edge surfaces spaced at a distance corresponding to the distance between said predetermined spaced parts and a contact surface transverse of said passageway between said edge surfaces and adapted to engage the central portion of a said staple;

means for positioning a said stable at said anvil with the central portion extending across said contact surface and the predetermined parts along the central portion at said edge surfaces, and the legs projecting along said edge surfaces and said guide surface;

a ram having a top side surface positioned along said guide surface, and spaced tip portions with a generally U-shaped opening therebetween defined by end surfaces disposed in a U-shaped pattern and generally at right angles to said guide surface, said end surfaces including an innermost surface generally parallel and opposed to said contact surface and opposed side surfaces generally parallel to said edge surfaces and spaced apart a distance exceeding the distance between said edge surfaces by about twice the thickness of the central portion of a said staple, said ram being mounted on said housing for movement from a first position affording positioning a said staple along said guide surface, to a second formed position with the side surfaces of said ram opposite the edge surfaces of said anvil to bend the staple closed around said anvil, the improvement wherein:

said edge surfaces of said anvil adjacent said guide surface each are disposed at an acute included angle of no less than 80 degrees with respect to said guide surface so that a said staple being bent around said anvil by said ram will remain generally in alignment with said guide surface until the staple is closed.

2. A stapler according to claim 1 wherein said acute included angle is between 83 and 87 degrees.

3. A stapler according to claim 1 wherein said acute included angle is about 85 degrees.

* * * * *